United States Patent [19]

Chopra

[11] Patent Number: 5,462,870
[45] Date of Patent: Oct. 31, 1995

[54] HUMAN DIPLOID SALIVARY GLAND EPITHELIAL CELL LINES

[75] Inventor: Dharam P. Chopra, Detroit, Mich.

[73] Assignee: Wayne State University, Detroit, Mich.

[21] Appl. No.: 52,263

[22] Filed: Apr. 23, 1993

[51] Int. Cl.$^6$ .................................. C12N 5/08; C12N 5/06
[52] U.S. Cl. .................................. 435/240.2; 435/240.1
[58] Field of Search .................................. 435/240.1, 240.2

[56] References Cited

U.S. PATENT DOCUMENTS

| | | | |
|---|---|---|---|
| 4,760,130 | 7/1988 | Thompson et al. | 530/350 |
| 4,980,290 | 12/1990 | Reznikoff et al. | 435/240.2 |
| 5,026,637 | 6/1991 | Soule et al. | 435/29 |
| 5,073,490 | 12/1991 | Babinet et al. | 435/240.2 |
| 5,132,222 | 7/1992 | Kanai et al. | 435/240.2 |

OTHER PUBLICATIONS

Soule et al., 1990, Cancer Research, vol. 50; pp. 6075–6086.
Paraskeva et al., 1988, Int. J. Cancer, 1988, vol. 41; pp. 908–912.
Freshney, 1987, Culture of Animal Cells, pp. 127–136, Alan R. Liss, Inc., New York.
Chopra, D. P., G. W. Taylor, P. A. Mathieu, B. Hukku and J. S. Rhim. "Immortalization of Human Tracheal Gland Epithelial Cells by Adenovirus 12–SV40 Hybrid Virus", *In Vitro Cell Develop. Biol.* 27A, 763–765, 1991.
Chopra, D. P., J. Wille and K. M. Siddiqui. "Propagation of Differentiating Normal Human Tracheobronchial Epithelial Cells In Serum–Free Medium". *J. Cell Physiol.* 130, pp. 173–181, 1987.
Chopra, D. P., R. L. Shoemaker, G. W. Taylor and P. A. Mathieu. "Characterization of Epithelial Cell Cultures Derived from Human Tracheal Glands", *In Vitro Cell. Dev. Biol.* 27A, 13–20, 1991.
Hayflick, L. and P. S. Moorhead. "The Serial Cultivation of Human Diploid Cell Strains", *Exp. Cell Res.* 25, 585–621, 1961.
Loo, D. T., J. I. Fujay, C. L. Rawson and D. W. Barnes. "Extended Culture of Mouse Embryo Cells Without Senescence: Inhibition by Serum", *Science,* 236, 20–202, 1987.
Masui, T., et al., "Type β Transforming Growth Factor is the Primary Differentiation–Inducing Serum Factor for Human Bronchial Epithelial Cells", *Proc. Nat. Acad. Sci. USA,* 83, 2438–2442, 1986.
Miyashita, M., et al., "Effects of Serum, Transforming Growth Factor Type B, or 12–O–Tetradecanoylphorbol–13–acetate on Ionized Cytosolic Calcium Concentration in Normal and Transformed Human Bronchial Epithelial Cells", *Cancer Res.,* 49, 63–67, 1989.
Moses, H. L., E. L. Branu, J. A. Proper and R. A. Robinson, "Transforming Growth Factor Production by Chemically Transformed Cells", *Cancer Res.* 41, 2842–2848, 1981.
Peterson, Jr., W. D., M. J. Ottenbreit and B. Hukku. "Isozyme Analysis in Cell Characterization", In: *Uses and Standarization of Vertebrate Cell Cultures,* Levine, E. M., R. E. Stevenson, M. K. Patterson, Jr., In Vitro Monograph, 5, 116–124, 1984.
Popescu, N. C. and J. A. Dipaolo. "Integration of Human Papilloma Virus 16DNA and Genomic Rearrangements in Immortalized Human Keratinocyte Lines", *Cancer Res.* 50, 1316–1323, 1990.
Rhim, J. S., J. Fujita, P. Arnstein and S. Aaronson. "Neoplastic Conversion of Human Keratinocytes by Adenovirus 12–SV40 Virus and Chemical Carcinogens", *Science* 232, 385387, 1986.
Stoner, G. D., M. E. Kaighn, R. R. Reddell, Resau, D. Boman, et al., "Establishment and Characterization of SV40 T–antigen Immortalized Human Esophageal Epithelial Cells", *Cancer Res.,* 51, 365–371, 1991.
Wolman, S. R., "Cancer Cytogenetics: Assumptions and Realities", In: *Cancer Cytogenetics.* (Willey, A. M. And Murphy, P. G., eds.), pp. 175–194, Wiley–Liss, Inc. 1991.
Zeitlin, P. L., L. Lu, J. Rhim, G. Cutting, G. Stetten, K. A., Kieffer, R. Craig and W. B. Cuggins. "A Cystic Fibrosis Bronchial Cell Line: Immortalization by Adeno–12–SV40 Infection", *Am. Respir. Cell Mol. Biol.,* 4, 313, 1991.
Peterson, Jr., W. D., W. F. Simpson, B. F. Hukku. "Cell Culture Characterization: Monitoring for Cell Identification", (Jacoby, W. B. and Pastan, I. H., eds.), *Methods of Enzymology,* vol. 58, New York, Academic Press, 1979, pp. 164–178.

*Primary Examiner*—Mindy B. Fleisher
*Assistant Examiner*—Nancy T. Vogel
*Attorney, Agent, or Firm*—Reising, Ethington, Barnard & Perry

[57] ABSTRACT

Described is a biologically pure culture of an immortal human parotid based epithelial cell. The present invention is concerned with the establishment in serum-free medium of normal diploid epithelial cell lines from the human parotid gland. The terms "diploid chromosome complement" mean that, as determined by karyotype analysis, the cells have neither gained or lost any chromosomes and do not appear to show any structural alterations.

2 Claims, 7 Drawing Sheets

FIG. IA
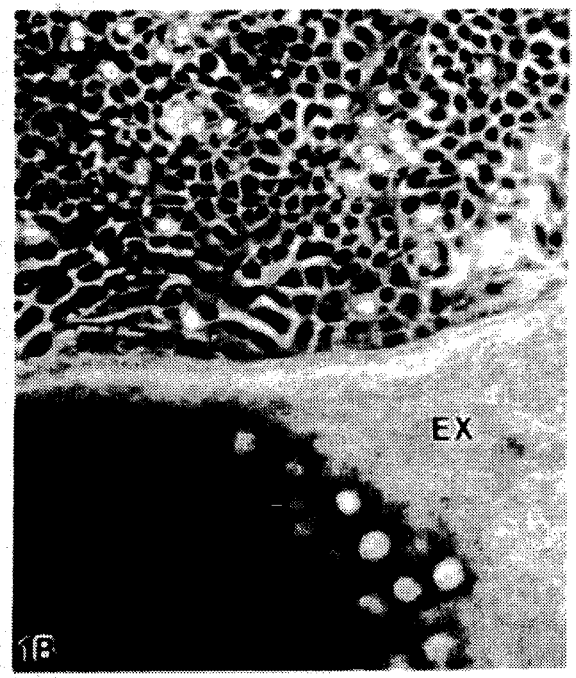
FIG. IB

HUMAN DIPLOID SALIVARY GLAND EPITHELIAL CELL LINES

This invention was made with United States Public Health Service Grant R01-DE-09591 from the National Dental Institute, National Institutes of Health.

TECHNICAL FIELD

The present invention relates to the establishment of normal human diploid epithelial cell lines derived from the human salivary parotid gland.

BACKGROUND OF THE INVENTION

Diploid human cells are believed to inherently exhibit limited life-span in vitro. Key evidence in support of the cellular senescence hypothesis was first reported by Hayflick and Moorhead about thirty years ago (Hayflick and Moorhead, 1961; Hayflick, 1979), who showed that diploid embryonic human lung fibroblasts in vitro could be cultivated for a short period and undergo only a limited, fixed number (50–60) of population doublings. It was further reported that the number of doublings that a cell population could survive was inversely related to the donor's age. Escape from senescence, which occurred mostly in cancer cells or experimentally transformed cells, was always accompanied by numerical and/or structural chromosomal alterations (Wolman, 1991); Fusenig et al. 1991). Immortality of cells has been induced by chemical carcinogens, oncogenes and viruses (Zeitlin et al. 1991, Chopra et al., 1991, Rhim et al. 1986, Stoner et al., Christian et al, 1987, Popescu and Dipaolo, 1990). All immortalized cell lines reported so far exhibit at least one transformed phenotype such as focus formation and/or anchorage independent growth (AIG) and certain relatively non-specific chromosomal aberrations. To date, there are no immortal epithelial cell lines which exhibit normal diploid chromosome complement.

Many investigators have utilized transformed epithelial cell culture models to investigate biochemical and molecular mechanisms of growth and differentiation, intercellular communications, toxicity and carcinogenicity of chemicals, oncogenes and cytokine expression, and activities of hormones. Results of these studies however, are severely flawed, because they are performed on cells exhibiting chromosomal aberrations involving undefined genetic alterations. Because of these chromosomal aberrations, the usefulness of transformed cells in research is greatly limited. For instance, if the cells have chromosomal alterations prior to a test treatment, it is difficult to determine specific genetic alterations associated with the treatment. For carcinogenesis studies, other investigators have used fibroblast cultures which usually can be propagated for longer duration than epithelial cells. However, the analogy between the two cell types (fibroblast and epithelial) is highly questionable because most cancers originate from cells of epithelial origin. More specifically, the lack of availability of diploid epithelial cells with an extended life-span has hindered cancer research in particular, and biomedical research in general.

In studies on propagation of epithelial cells in vitro, serum is frequently employed as a growth supplement. More recent studies have demonstrated that serum contains numerous undefined growth inhibitory and toxic factors. For example, TGF-β, a major component of serum, has been shown to inhibit the growth of a variety of cell types (Masui et al., 1986, Loo et al., 1987, Miyashita et al., 1989). Additionally, high concentrations of proteases and chelating agents are repeatedly used for serial passaging of cell cultures and may also cause irreparable damage to cells. Thus, it is not surprising that continuous culturing of cells in serum-containing medium and repeated treatments with proteases and chelating agents ultimately causes the death of normal cells.

U.S. Pat. No. 4,980,290 entitled "Human Uroepithelial Cell" describes cell lines derived from the human ureters and immortalized by SV40 virus; those cells show preneoplastic phenotypes and gross chromosomal aberrations and they are maintained in serum-supplemented medium. U.S. Pat. No. 5,026,637 entitled "Immortal Human Mammary Epithelial Cell Lines" are maintained in serum-supplemented medium and show numerous chromosomal aberrations including several marker chromosomes. Neither of the processes described, nor the cells themselves, constitute normal human diploid immortal epithelial cell lines.

Therefore, it is most desirable to provide normal human epithelial cell lines which maintain a normal diploid chromosomal complement, produce tissue-specific proteins, and that could be cultivated indefinitely. It would also be desirable to provide such cell lines which could be cultivated in serum-free medium. It would be further desirable to provide such cell lines without infection and/or transfection with a virus and/or exogenous DNA. Such cell lines would be most desirable to the studies on carcinogenesis, aging, growth and differentiation, and to determine sensitivity to suspected reactive agents on a long-term basis. The present invention meets these objectives and provides two epithelial cell lines, HPAM1 and HPAF1, derived from the normal human salivary parotid gland, which maintain a normal diploid chromosome complement, produce the tissue-specific proteins amylase and proline-rich protein (PRP), and are cultivated indefinitely in serum-free medium. The invention also describes the process for preparing epithelial cells in such a manner so as to obtain the immortal salivary parotid gland cell lines.

SUMMARY OF THE INVENTION

The present invention is concerned with the establishment in serum-free medium of normal diploid epithelial cell lines from the human parotid gland. The terms "diploid chromosome complement" mean that, as determined by karyotype analysis, the cells have neither gained or lost any chromosomes and do not appear to show any structural alterations.

In one aspect of this invention, there is provided two diploid epithelial cell lines, HPAM1 and HPAF1 derived from a normal human male and a female salivary parotid gland, respectively. These novel cell lines are propagated in serum-free medium, have an indefinite life-span and lack transformed phenotypes. The cell lines are capable of being preserved cryogenically. The novel cell lines, established by modification of culture conditions and without infection and transfection with oncogenic DNA, exhibit diploid chromosome complement, keratin positive titers and produce tissue-specific proteins including α-amylase and PRP. Specifically, the invention provides immortalized diploid epithelial cell lines of human salivary gland, a novel method to develop such cell lines, and the usefulness of the novel cells in biomedical research and industry.

In another aspect of the invention, there is provided the procedure for generating long-term epithelial cell lines of human tissues.

Hence, the object of the present invention is to provide two diploid epithelial cell lines, HPAM1 and HPAF1 derived from normal parotid gland, which are to be used in experimental studies in carcinogenesis, aging, growth and differentiation.

The invention is concerned with a male epithelial immortal cell culture that has been deposited with and assigned by American Type Culture Collection (ATCC) with the No. CRL11706.

The invention is also concerned with a female immortal epithelial cell culture that has been deposited with and assigned by ATCC with the No. CRL11707.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1A is a parotid gland explant comprised of acinar structures used for explant-outgrowth cultures. Bar=18.5 μm.

FIG. 1B is an outgrowth culture in close proximity to an explant (EX), epithelial cells show mainly polygonal morphology. Bar=18.5 μm.

DESCRIPTION OF THE PREFERRED EMBODIMENTS

Figure 2A:
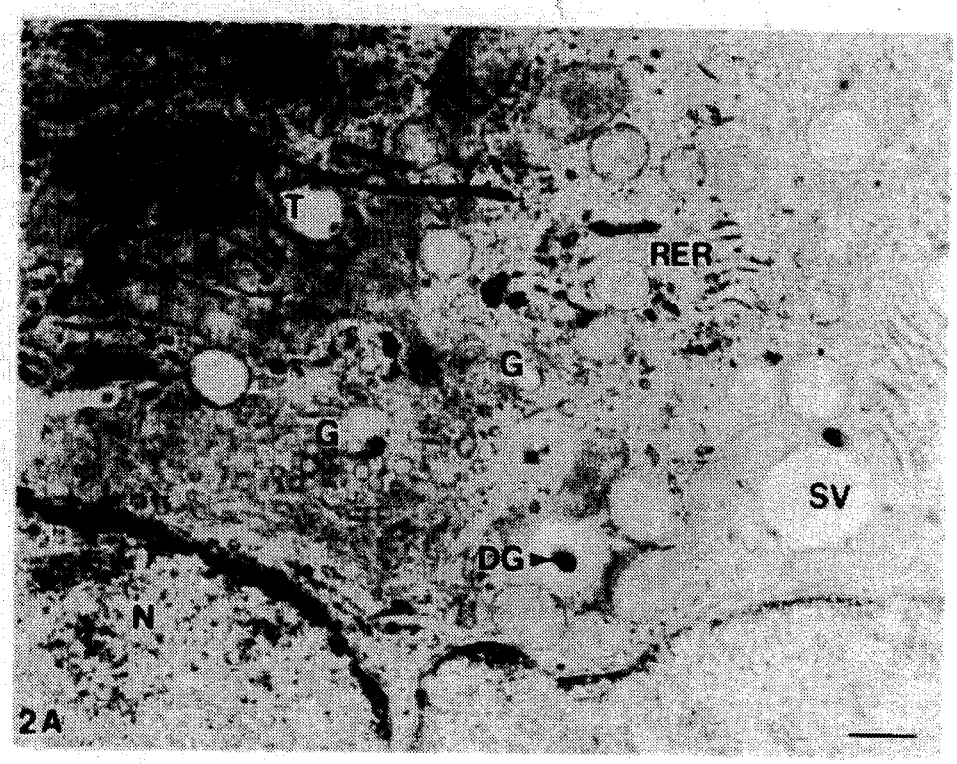
FIG. 2A is transmission electron micrograph of a 3rd passage culture illustrating epithelial characteristics. Tonofilament bundles (T), secretory vesicles (SV), Golgi (G), rough endoplasmic reticulum (RER), dense granules (DG). Bar–0.43 μm.
Figure 2B:
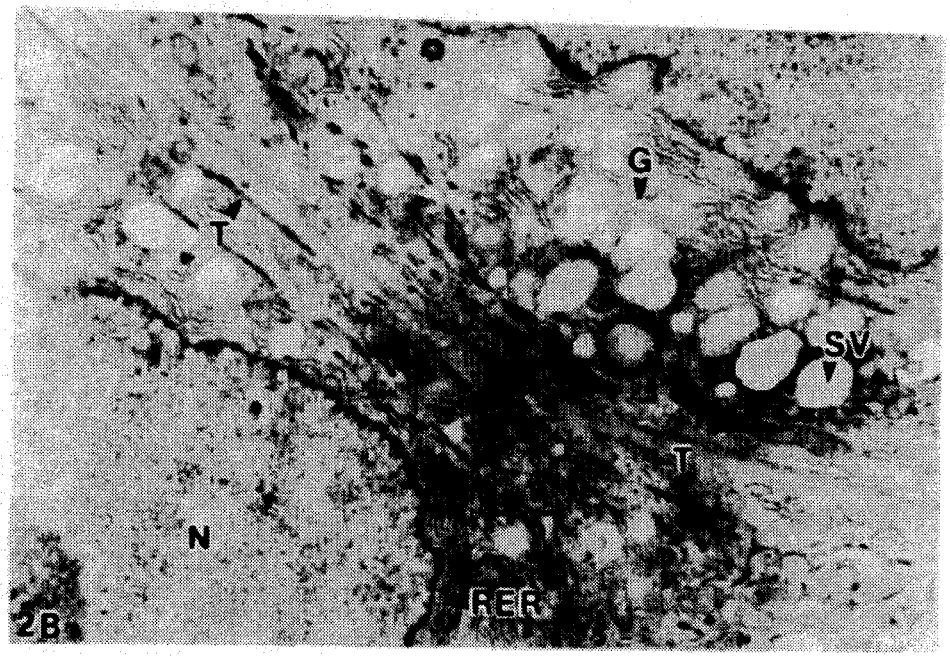
FIG. 2B is a transmission electron micrograph of a passage 35 culture. The cells exhibit many epithelial cell characteristics including SV, G, T, and RER. Bar =0.53 μm.

The invention provides an epithelial cell line HPAM1 derived from a normal male salivary parotid gland. The cell line is cultivated indefinitely in serum-free medium, exhibits a normal diploid chromosome complement, and produces the tissue-specific proteins, α-amylase and PRP. HPAM1 has been deposited with the American Type Culture Collection under the registration number CRL11706.

The invention provides a second epithelial cell line HPAF1 derived from a normal female salivary parotid gland. The cell line is cultivated indefinitely in serum-free medium, exhibits a normal diploid chromosome complement, and produces the tissue-specific proteins, α-amylase and PRP. HPAF1 has been deposited with the American Type Culture Collection under the registration number CRL11707.

The invention also provides the details of the procedure to initiate and establish the above-mentioned cell lines.

Described below are the various steps that were utilized to obtain HPAM1 and HPAF1.

Tissue Procurement and Culture. Specimens of normal human parotid gland were obtained at surgery (Tissue Procurement Service, University of Alabama, Birmingham, Ala.). Two specimens were employed for the cell lines described in here. One specimen was obtained from a 73 year old male, and the second tissue was obtained from a 40 year old female.

The tissues were placed in cold RPMI (Roswell Park Memorial Institute) medium, supplemented with antibiotics; penicillin (100 U/ml), streptomycin (100 μm/ml), and fungizone (0.25 μg/ml) and transported via overnight mail. On receipt, the tissue was thoroughly rinsed in Leibowitz's L-15 medium (Gibco, Grand Island, N.Y.). Under a dissecting microscope, explants (approximately 1 mm×1 mm) composed of acinar tissue were cut out and primary cultures prepared by the explant-outgrowth method (Chopra et al., 1987, 1991, incorporated herein by reference) in serum-free medium comprised of KBM (Keratinocyte Basal Medium, Clonetics, San Diego, Calif.), supplemented with insulin (5 μg/ml, Sigma), hydrocortisone (0.5 μg/ml), EGF (epidermal growth factor)(10 ng/ml), bovine pituitary extract (25 μg/ml), penicillin (100 IU/ml) and streptomycin (100 μg/ml, Gibco). The $Ca^{2+}$ concentration of the KBM was 0.15 mM. For passaging, primary outgrowths were rinsed in $Ca^{2+}$ and $Mg^{2+}$ − free Hanks' balanced salt solution (HBSS) and treated with 0.125% trypsin solution in HBSS. The dissociated cells were removed and suspended in KBM containing 5% fetal bovine serum (Gibco) to inactivate the trypsin. The cell suspension was centrifuged at 1000×g at 4° C. for 10 minutes. Finally, the pellet was resuspended in serum-free complete medium and dispensed into tissue culture dishes. Complete medium is of KBM supplemented with insulin (5 μg/ml), hydrocortisone (0.5 μg/ml), EGF (10 ng/ml), bovine pituitary extract (25 μg/ml), penicillin (100 IU/ml), and streptomycin (100 μg/ml). Cell cultures were maintained at 37° C. in an atmosphere of 5% $CO_2$ in air. The medium was changed three times per week. The cells were propagated on collagen-coated (Vitrogen) dishes (Celtrix, Palo Alto, Calif.) in the complete medium.

Epithelial Characteristics of Cell Culture

Morphological Characterization. The epithelial nature and salivary gland origin of the cells was established by ultrastructural, immunocytochemical and biochemical analyses. For electron microscopy, cultures were fixed in 1% glutaraldehyde in 0.1M cacodylate buffer for at least 2 hours and post-fixed in 1% osmium tetroxide. The cultures were dehydrated in graded concentrations of ethanol and embedded in situ with Polybed 812 (Polysciences, Warrington, Pa.). Embedded cultures were thin-sectioned with a diamond knife, stained in uranyl acetate and lead citrate, and observed in a Zeiss transmission electron microscope.

Cytokeratins. The occurrence of cytokeratins is a characteristic feature of epithelial cells. Cultures were examined immunocytochemically with α-keratin antiserum. Cells grown on 12-mm glass cover-slips were washed with phosphate-buffered saline (PBS, Gibco), fixed with cold methanol for 4 minutes, and allowed to dry. The coverslips were then incubated with anti-α-keratin antiserum 1:40 (guinea pig, Sigma) for 30 minutes. The cultures were washed with PBS and then incubated with fluorescein isothiocyanate-conjugated (FITC) rabbit anti-guinea pig IgG 1:80 (Sigma). Thirty minutes later, the cultures were washed three times with PBS, mounted in PBS:glycerol (50:50 v/v), and observed in a Nikon fluorescence microscope.

Amylase and PRP. The major secretory products of the parotid gland acinar cell are α-amylase and PRP. Production of these proteins by the cell cultures was determined immunocytochemically as described above for cytokeratins. The α-amylase antibody was obtained from Sigma (St. Louis, Mo.). The PRP antibody was obtained from Dr. Michael Levine (State University of New York, Buffalo, N.Y.). The primary antibodies were used at about a 1:100 dilution. Secondary antibody was used at a 1:40 dilution.

Growth Characterization. Growth characteristics were examined at different passages. The cells were plated at a density of $1 \times 10^{3.5}$ mm dish in the complete medium. For each experiment, about 18 cultures were prepared. Twenty-four hours later, a group of three cultures were terminated and the cell number in each culture counted using the hemacytometer and the trypan blue exclusion method. The mean and standard deviation was then determined. This 24 hour count served as the plating efficiency for the cell culture. Groups of three cultures each were then terminated at different periods after plating and cell number determined for each group. The cell population doublings and the population doubling times were determined as described previously (Chopra et al., 1991).

Immortalized cells usually acquire the ability to grow in suspension in semi-solid medium. To test anchorage independent growth, the soft agar method of Moses et al (Moses et al, 1981) was used. Two-layer agar plates were prepared in 35 mm culture dishes by first applying a bottom layer of 0.8% agar in complete medium. After the bottom layer had set, a top layer of 0.4% agar, containing $8 \times 10^3$ cells was added and the cultures were incubated at 37° C. in 5% $CO_2$ in air. On the tenth day after plating, cultures were fed with 1 ml of complete medium. Twenty-six days after plating, the cultures were stained for 24 hours with 1.5% 2-(p-iodophenyl)-3-(p-nitrophenyl)-4-phenyltetrazolium chloride solution in 0.9% NaCl, and the formation of cell colonies was examined and enumerated.

Karyotype Analyses. Preparation of cells for cytogenetic analysis followed the method previously described (Paterson, et al., 1979, 1984). Exact chromosome counts were made on thirty metaphases. TrypsinGiemsa banded metaphases were photographed and karyotypes prepared. Isozyme analysis was carried out according to Peterson et al, (1984) on certain polymorphic isozymes.

Cryopreservation and Cell Recovery. Monolayer cultures are dissociated with 0.125% trypsin as described above, the cells are pelleted by centrifugation at 1000 RPM at 4° C. for 10 minutes. The pellet is resuspended in the cold freeze medium comprised of the complete medium (described above) supplemented with 5% fetal bovine serum and 5% dimethyl sulfoxide (DMSO). The concentration of the cell suspension is adjusted to $1 \times 10^6$ cells/ml. Then 1.5 ml of the cell suspension is dispensed in each cryovial. The vials are tightly closed and placed in a programmed freezer. Generally, precooled cells are cooled further at a rate of 1°–3° C. per minute to −30° C. At this point, a more rapid drop in temperature is programmed (20°–30° C./min) until the temperature reaches to about −150° C. The vials are then transferred from the freezer chamber to the storage chamber in liquid nitrogen (−180/−190° C.).

For cell recovery, vials are removed from the liquid nitrogen storage freezer and placed into a water bath at 37–39° C. Special precautions are taken to use protective masks and gloves while removing vials from the liquid nitrogen. Immediately after thawing, the vials are immersed in 70% ethanol at room temperature. All procedures from this point on are carried out under strict aseptic conditions. Cell suspensions are then removed from the vials and diluted with serum-free growth medium. The cell suspension is then centrifuged, cell pellet resuspended in the growth medium and plated on collagen coated culture dishes.

Results

Two tissue specimens were used, one derived from a male and the second from a female. FIG. 1A shows that explants used for initiating primary cultures consisted essentially of acinar tissue. Explants of both tissues yielded outgrowth cultures comprised primarily of epithelial cells (FIG. 1B). Ultrastructural examination of primary cultures showed numerous microvilli on cell surfaces and sparsely distributed desmosomal junctions between them. Their cytoplasm contained prominent tonofilament bundles and numerous, mainly perinuclear, secretory vesicles which were frequently membrane-bound (FIG. 2A). The cellular organelles, including rough endoplasmic reticulum (RER) and Golgi complexes were prominent. At higher passages, cellular ultrastructure remained unchanged and exhibited secretory cell characteristics.

Figure 3:
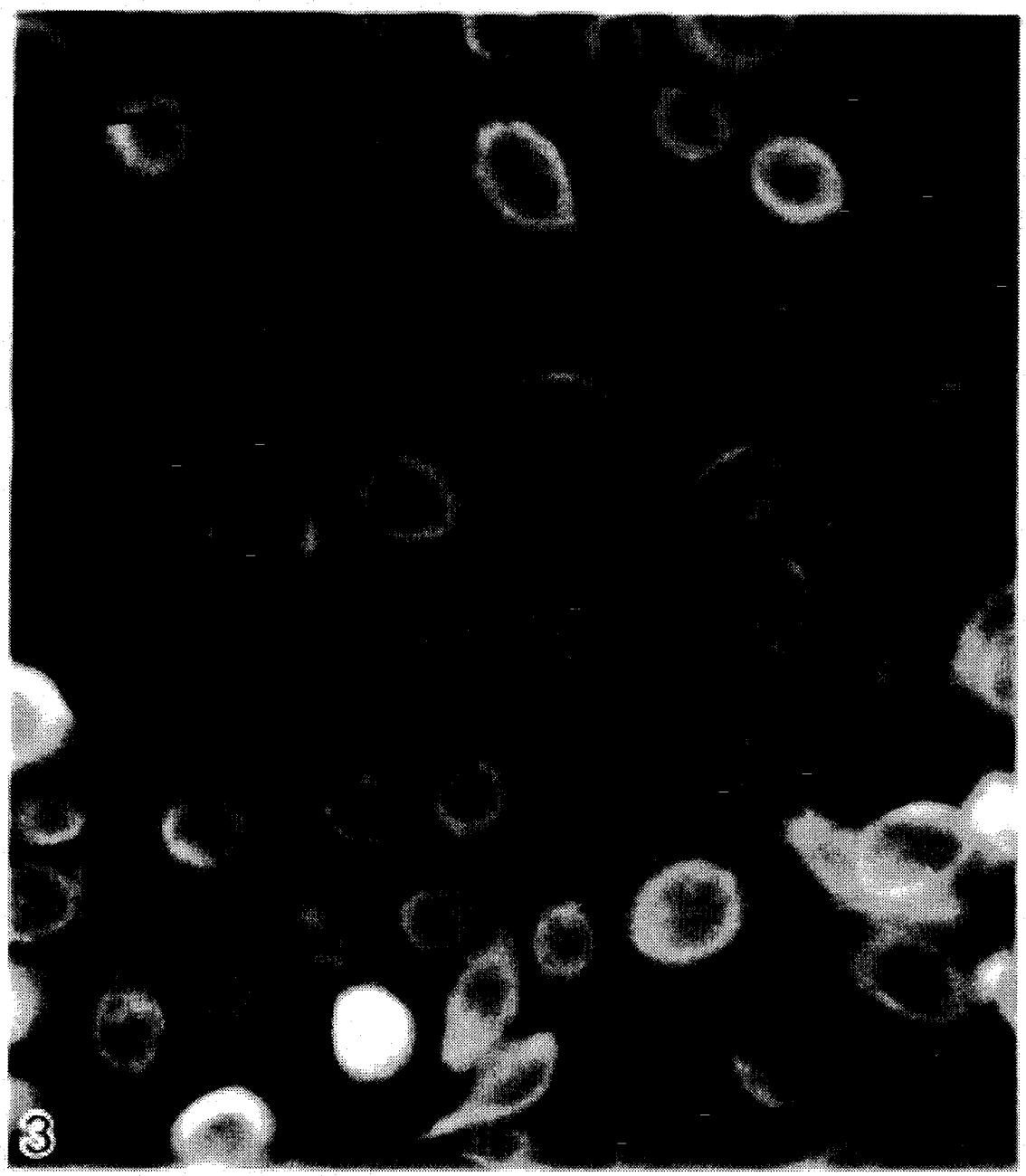
FIG. 3 demonstrates indirect immunofluorescent reaction of HPAM1 (passage 50) with an anti-keratin antibody. All cells show a positive reaction. HPAF1 cell line showed a similar strong reaction (not shown). Bar =6.5 μm.

The occurrence of cytokeratins was examined at different passages. FIG. 3 shows immunocytochemical reaction for cytokeratins in a passage 50 culture. All cells were found to show a positive reaction. The staining reaction formed a filamentous pattern, as keratins, present mainly in epithelial cells, are a major component of intermediate filaments. Cells from both cell lines showed a strong reaction for keratins.

Figure 4A:
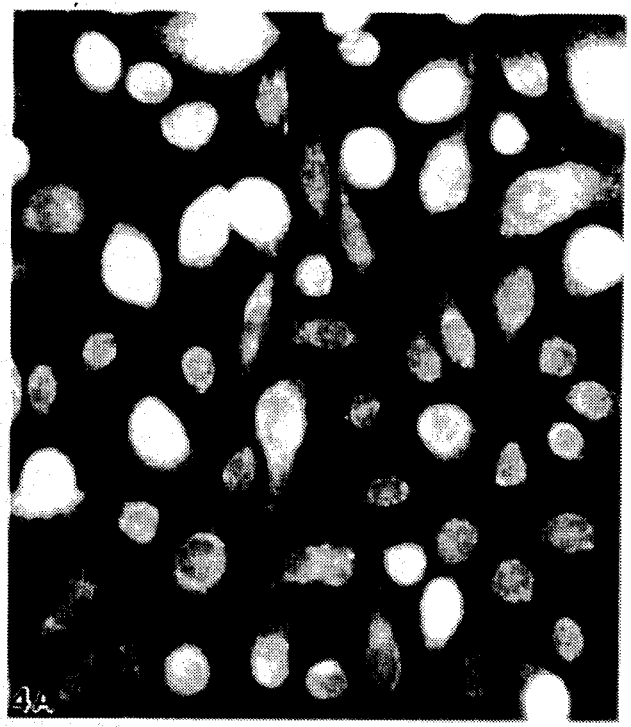
FIG. 4A shows indirect immunofluorescent reaction of HPAM1 (passage 35) with anti-amylase anti-body. All cells exhibit a positive reaction which was predominant in the perinuclear region. HPAF1 showed similar reaction (not shown). Bar=6.5 μm.
Figure 4B:
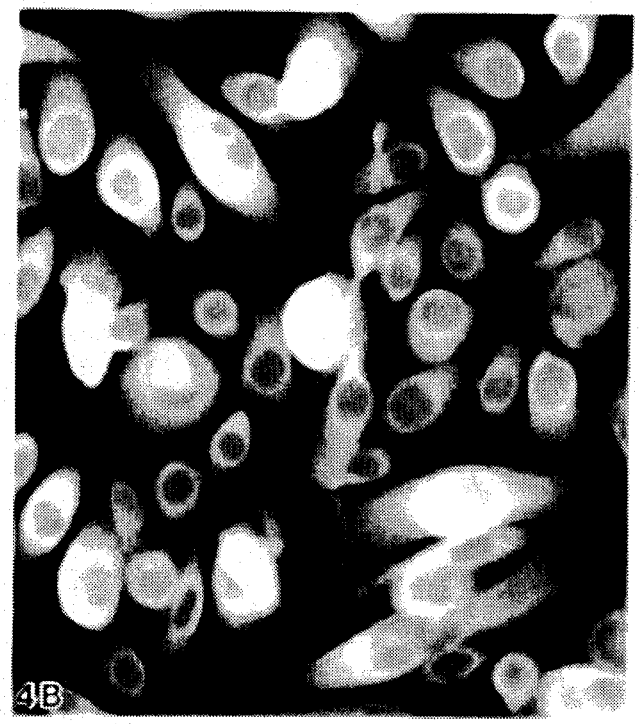
FIG. 4B shows indirect immunofluorescent reaction of HPAM1 (passage 75) with anti-PRP antibody. All cells exhibit positive reaction. HPAF1 showed similar reaction (not shown). Bar=0.65 μm.
Figure 5A:
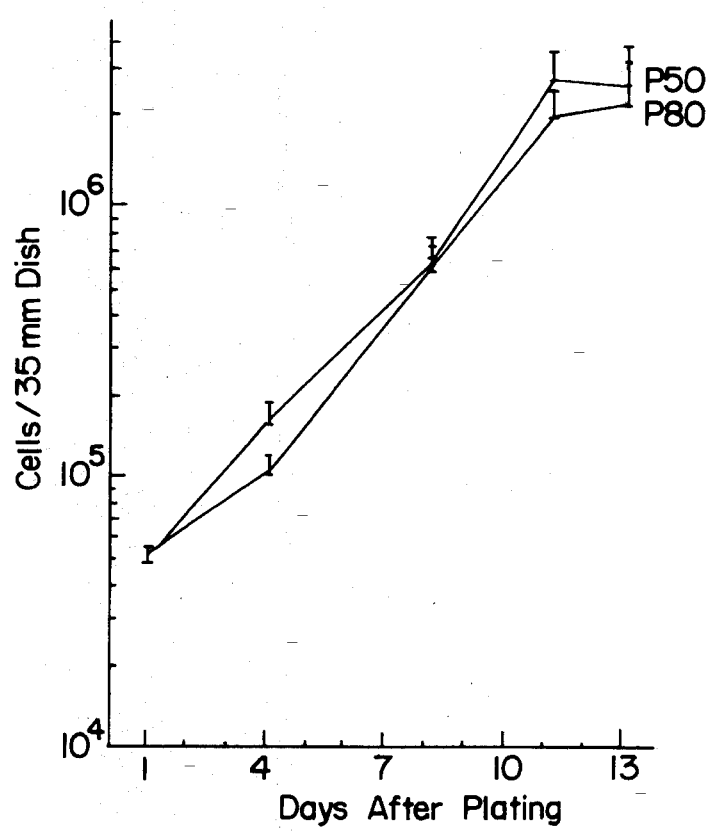
FIG. 5A shows growth curves of HPAM1 at passages 50 and 80.

Reactions for α-amylase and PRP were examined at different passages. Strong positive reactions were observed both for α-amylase and PRP (FIGS. 4A,B). The reactions were predominant in perinuclear locations which contained Golgi complexes. Negative controls, cultures not reacted with primary antibodies, showed no staining (not shown). The cell lines derived from the male and female salivary glands have been designated as HPAM1 and HPAF1, respectively. FIG. 5A shows growth curves of HPAM1 at passages 50 and 80. At both passages, the plating efficiency was approximately 40%; their cell population doubling times were approximately 48 and 38 hours, respectively. Currently, HPAM1 is propagating at 84th passage and has undergone approximately 330 accumulative population doublings (FIG. 5B).

Figure 5C:
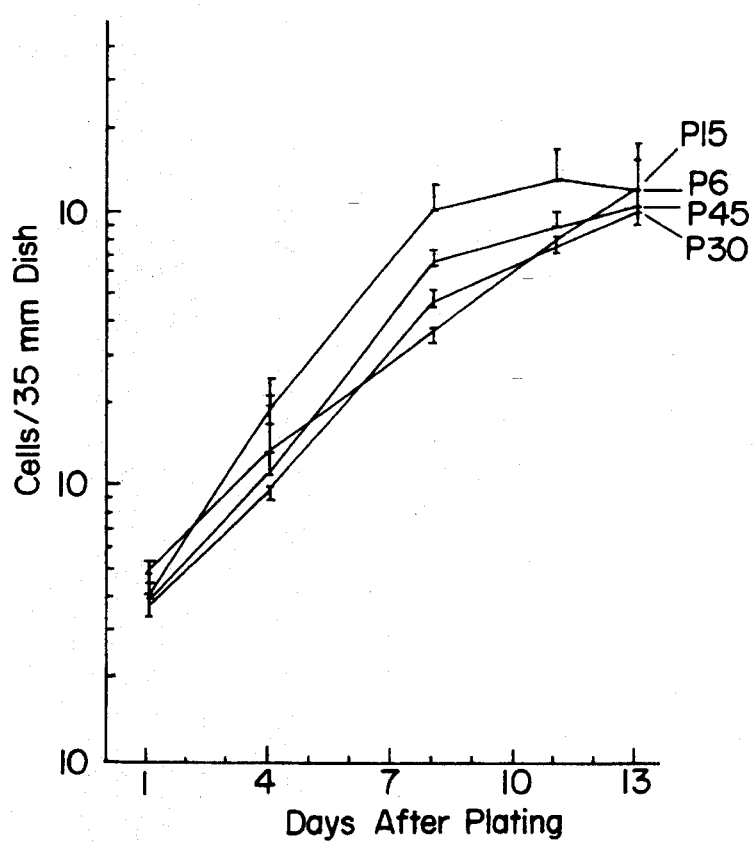
FIG. 5C shows growth curves of HPAF1 at different passages.
Figure 5B:
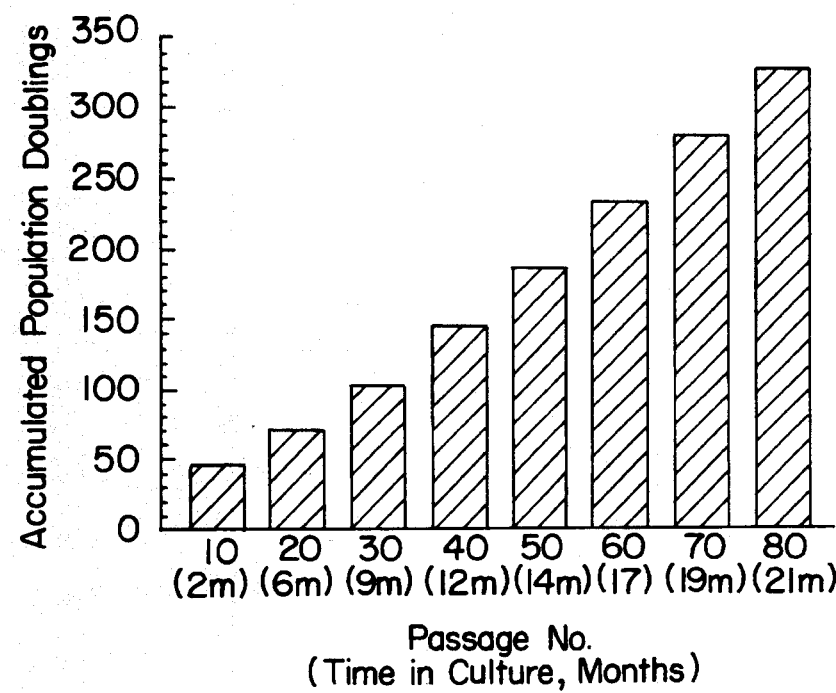
FIG. 5B shows accumulated population doublings of HPAM1 up to passage 80.
Figure 5D:
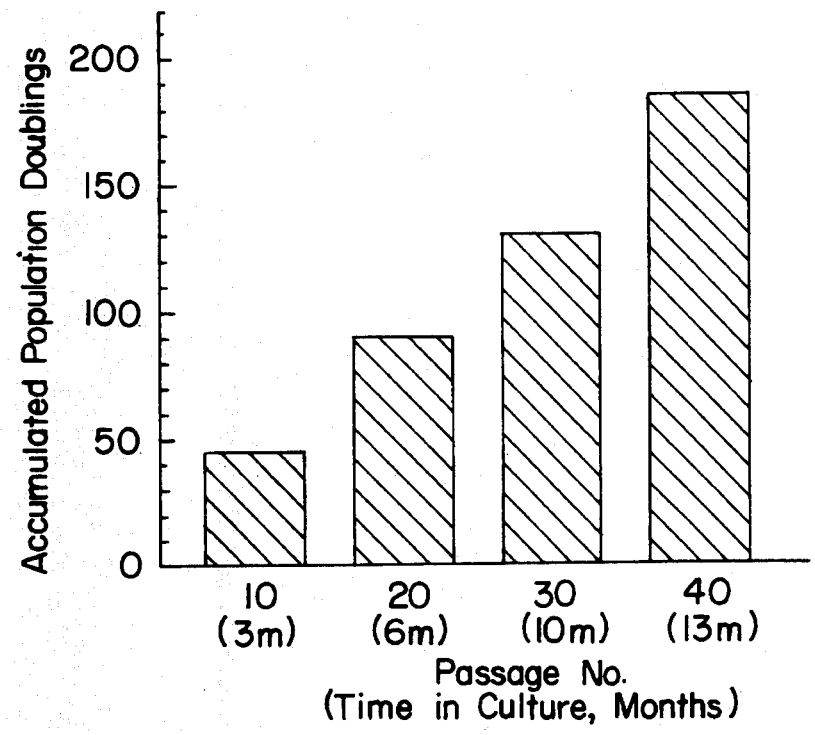
FIG. 5D shows accumulative population doublings of HPAF1 up to passage 40.

At passages 15 and 30, the plating efficiency of HPAF1was approximately 50% and 35% and the doubling time about 39 and 43 hours, respectively (FIG. 5C). The cell line is currently propagating at the 46th passage and has undergone approximately 194 population doublings (FIG. 5D).

Figure 6A:
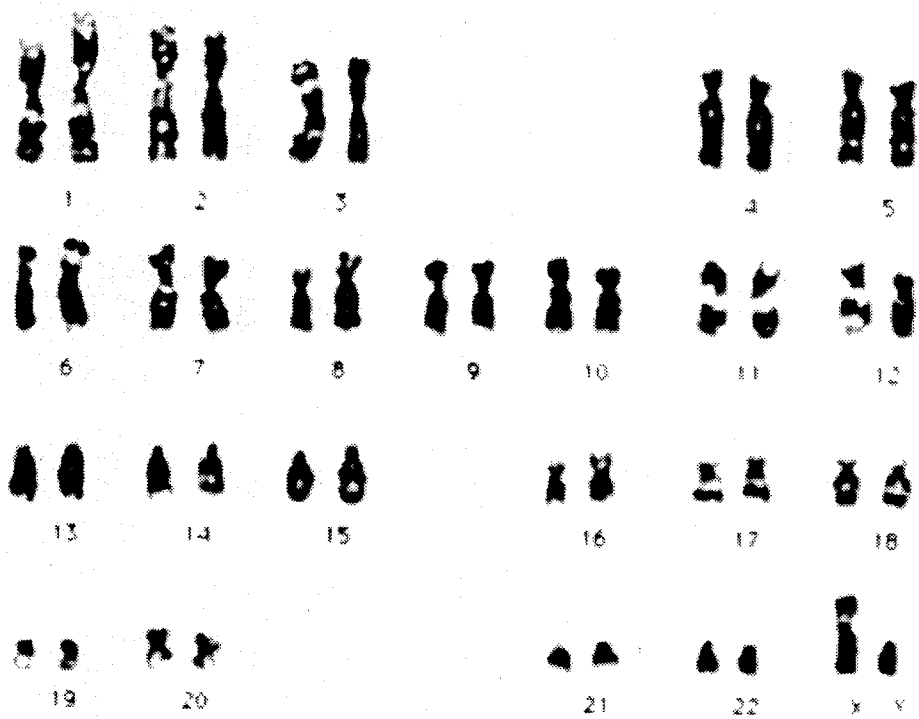
FIG. 6A shows a normal diploid karyotype of HPAM1 (46,XY) at passage 50. (189 population doublings)

For HPAM1 , one of the karyotypes was performed at passage 50 (about 189 population doublings). Thirty metaphases were analyzed. The modality was 46 (46, XY), thirty-one metaphases had 46, seven had 45 and two had 47 chromosomes. Seven karyotypes were prepared. Six of them had 46 chromosomes and one had 45. The cells with 45 and 47 chromosomes probably represent random loss and gain of a chromosome. FIG. 6A shows a typical diploid karyotype of a passage 50 cell of the HPAM1 cell line. It has X and Y chromosomes and shows a normal diploid complement.

Figure 6B:
FIG. 6B shows normal diploid karyotype (46,XX) of HPAF1 at passage 37 (170 population doublings). No chromosomal structural alterations were noted.

For cell line HPAF1, karyotype analysis was performed on passage 37 (approximately 170 population doublings). Thirty metaphases were analyzed. The modal number was 46; twenty-eight metaphases had 46 chromosomes, two metaphases had 45. FIG. 6B shows a typical karyotype of HPAF1. It has two normal XX chromosomes, and shows normal diploid human female chromosomal complement (46,XX). Currently, the cell line is at 46th passage.

From the results above, it can be appreciated that HPAM1 and HPAF1 are unique cell lines of human epithelial origin, exhibit diploid karyotype and are propagated in serum-free medium. Because the cell lines have been stably maintained for an indefinite duration, they provide models for studies in carcinogenesis, aging, growth and differentiation and for testing the effects of long-term exposure of epithelial cells in vitro to substances of undefined toxicity. Further, the HPAM1 and HPAF1 cell lines could serve as expression systems for transfected genes and for the development of vaccines for use in humans.

While the form of the invention herein disclosed constitutes presently preferred embodiments, many others are possible. It is not intended herein to mention all of the possible equivalent forms or ramifications of the invention.

It is understood that the terms used herein are merely descriptive rather than limiting, and that various changes may be made without departing from the spirit or scope of the invention.

References

Chopra, D. P., G. W. Taylor, P. A. Mathieu, B. Hukku and J. S. Rhim. Immortalization of human tracheal gland epithelial cells by adenovirus 12-SV40 hybrid virus. In Vitro Cell Develop. Biol. 27A, 763–765, 1991.

Chopra, D. P., J. Wille and K. M. Siddiqui. Propagation of differentiating normal human tracheobronchial epithelial cells in serum-free medium. J. Cell Physiol. 130, 173–181, 1987.

Chopra, D. P., R. L. Shoemaker, G. W. Taylor and P. A. Mathieu. Characterization of epithelial cell cultures derived from human tracheal glands. In Vitro Cell. Dev. Biol. 27A, 13–20, 1991.

Christian, B. J., L. J. Loretz, T. D. Oberly and C. A. Reznikoff. Characterization of human uroepithelial cells immortalized in vitro. Cancer Res. 47, 6066–6073, 1987.

Fusenig, P., D. Boukamp, Breitkreutz and A. Hulsen. Altered regulation of growth and differentiation at different stages of transformation of human skin keratinocytes. In: Neoplastic Transformation in Human Cell Culture-Mechanisms of Carcinogenesis (J. S. Rhim and A. Dritschilo, eds.) Humana Press, Totowa, NJ, pp 235–250, 1991.

Hayflick, L. and P. S. Moorhead. The serial cultivation of human diploid cell strains. Exp. Cell Res. 25, 585–621, 1961.

Hayflick, L. The cell biology of human aging. New England J. Med. 19, 1302–1308, 1979.

Loo, D. T., J. I. Fujay, C. L. Rawson and D. W. Barnes. Extended culture of mouse embryo cells without senescence: Inhibition by serum. Science 236, 200–202, 1987.

Masui, T., L. M. Wakefield, J. F. Lechner, M. A. LaVeck and M. B. Sporn. Type $\beta$ transforming growth factor is the primary differentiation-inducing serum factor for human bronchial epithelial cells. Proc. Natl. Acad. Sci. USA 83, 2438–2442, 1986.

Miyashita, M., M. W. Smith, J. C. Willey, J. F. Lechner, B. F. Trump, C. C. Harris. Effects of serum, transforming growth factor type ,B, or 12-0-tetradecanoylphorbol-13-acetate on ionized cytosolic calcium concentration in normal and transformed human bronchial epithelial cells. Cancer Res. 49, 63–67, 1989.

Moses, H. L., E. L. Branum, J. A. Proper and R. A. Robinson. Transforming growth factor production by chemically transformed cells. Cancer Res. 41, 2842–2848, 1981.

Peterson, Jr., W. D., M. J. Ottenbreit and B. Hukku. Isozyme analysis in cell characterization. In: Uses and Standardization of Vertebrate Cell Cultures. Levine, E. M., R. E. Stevenson. M. K. Patterson, Jr. In Vitro Monograph 5, 116–124, 1984.

Peterson, Jr., W. D., W. F. Simpson, B. F. Hukku. Cell culture characterization: Monitoring for Cell Identification. (Jakoby, W. B. and Pastan, I. H., eds.) Methods of Enzymology. Vol. 58, New York, Academic Press, 1979, pp 164–178.

Popescu, N. C. and J. A. Dipaolo. Integration of human papilloma virus 16DNA and genomic rearrangements in immortalized human keratinocyte lines. Cancer Res. 50, 1316–1323, 1990.

Rhim, J. S., J. Fujita, P. Arnstein and S. Aaronson. Neoplastic conversion of human keratinocytes by adenovirus 12-SV40 virus and chemical carcinogens. Science 232, 385387, 1986.

Stoner, G. D., M. E. Kaighn, R. R. Reddell, Resau, D. Boman, et al. Establishment and characterization of SV40 T-antigen immortalized human esophageal epithelial cells. Cancer Res. 51, 365–371, 1991.

Wolman, S. R. Cancer cytogenetics: Assumptions and realities. In: Cancer Cytogenetics. (Willey, A. M. and Murphy, P. G., eds.) pp. 175–194, Wiley-Liss, Inc. 1991.

Zeitlin, P. L., L. Lu, J. Rhim, G. Cutting, G. Stetten, K. A. Kieffer, R. Craig and W. B. Guggins. A cystic fibrosis bronchial cell line: Immortalization by adeno-12-SV40 infection. Am. Respir. Cell Mol. Biol. 4, 313, 1991.

What is claimed is:

1. A biologically pure culture of a normal diploid immortal epithelial cell line derived from a male human designated ATCC Registration No. CRL11706.

2. A biologically pure culture of a normal diploid immortal epithelial cell line derived from a female human designated ATCC Registration No. CRL11707.

* * * * *